United States Patent
Wagner et al.

(10) Patent No.: US 8,343,102 B2
(45) Date of Patent: Jan. 1, 2013

(54) FLUID DRIVEN MEDICAL INJECTORS

(75) Inventors: Gary S. Wagner, Independence, KY (US); Frank M. Fago, Mason, OH (US); Peter Staats, Loveland, OH (US); Dane Battiato, Franklin, TN (US)

(73) Assignee: Mallinckrodt LLC, Hazelwood, MO (US)

( * ) Notice: Subject to any disclaimer, the term of this patent is extended or adjusted under 35 U.S.C. 154(b) by 170 days.

(21) Appl. No.: 12/830,546

(22) Filed: Jul. 6, 2010

(65) Prior Publication Data

US 2010/0274127 A1 Oct. 28, 2010

Related U.S. Application Data

(62) Division of application No. 12/665,741, filed as application No. PCT/US2008/072978 on Aug. 13, 2008.

(60) Provisional application No. 60/965,364, filed on Aug. 20, 2007.

(51) Int. Cl.
*A61M 37/00* (2006.01)
*A61M 1/00* (2006.01)
*A61K 9/22* (2006.01)
*F04B 39/06* (2006.01)

(52) U.S. Cl. ........ 604/131; 604/151; 604/152; 604/140; 604/141; 604/890.1; 417/438

(58) Field of Classification Search ............... 604/131, 604/151, 152, 154, 246, 247, 143, 890.1, 604/892.1, 140, 141; 600/432; 417/438
See application file for complete search history.

(56) References Cited

U.S. PATENT DOCUMENTS

| | | | |
|---|---|---|---|
| 4,085,749 A | 4/1978 | Chambron | |
| 4,150,672 A | 4/1979 | Whitney et al. | |
| 4,235,234 A | 11/1980 | Whitney et al. | |
| 4,250,887 A | 2/1981 | Dardik et al. | |
| 4,273,122 A | 6/1981 | Whitney et al. | |
| 4,320,757 A | 3/1982 | Whitney et al. | |
| 4,861,340 A | 8/1989 | Smith et al. | |
| 4,944,726 A | 7/1990 | Hilal et al. | |
| 5,197,322 A | 3/1993 | Indravudh | |
| 5,354,273 A | 10/1994 | Hagen | |
| 5,505,707 A * | 4/1996 | Manzie et al. | 604/131 |
| 5,571,261 A | 11/1996 | Sancoff et al. | |
| 6,306,117 B1 | 10/2001 | Uber, III | |
| 6,881,043 B2 | 4/2005 | Barak | |
| 7,566,320 B2 * | 7/2009 | Duchon et al. | 604/131 |
| 2003/0236498 A1 | 12/2003 | Gross et al. | |
| 2004/0133186 A1 | 7/2004 | Joshi | |
| 2004/0199116 A1* | 10/2004 | Trompen et al. | 604/131 |
| 2005/0192561 A1 | 9/2005 | Mernoe | |

FOREIGN PATENT DOCUMENTS

| | | |
|---|---|---|
| DE | 198 18 646 A1 | 10/1999 |
| FR | 2 131 077 | 11/1972 |
| FR | 2 505 190 | 11/1982 |
| WO | WO 97/28835 | 8/1997 |
| WO | WO 02/064194 | 8/2002 |
| WO | WO 2005/046756 | 5/2005 |

* cited by examiner

*Primary Examiner* — Kevin C Sirmons
*Assistant Examiner* — Bradley G Thomas, Jr.
(74) *Attorney, Agent, or Firm* — Marsh, Fischmann, Breyfogle LLP

(57) ABSTRACT

Some injectors of the invention may include a fluid drive responsive to pressure of a working fluid (e.g., liquid, pneumatic, or both) to impart a sequence of forces to drive a delivery device (e.g., a syringe) to deliver a medical fluid (e.g., a contrast agent, a radiopharmaceutical, a drug, or a combination thereof). Some injectors may include a multimedia tube configured to pass a working fluid (e.g., air) and a light signal (e.g., infrared). Some injectors may include a peristaltic drive responsive to pressure of a working fluid.

9 Claims, 8 Drawing Sheets

FLUID DRIVEN MEDICAL INJECTORS

RELATED APPLICATIONS

This application is a divisional of U.S. patent application Ser. No. 12/665,741 entitled FLUID DRIVEN MEDICAL INJECTORS filed on 21 Dec. 2009, and claims priority to U.S. provisional application Ser. No. 60/965,364 filed on 20 Aug. 2007 entitled FLUID DRIVEN MEDICAL INJECTORS.

FIELD OF THE INVENTION

The present invention relates generally to medical fluid injectors and, more particularly, to contrast media injectors used in medical imaging procedures

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In various medical modalities, a powered injector is used to inject the patient with a medical fluid, such as a drug, a contrast agent, a radiopharmaceutical, or a combination thereof. A typical powered injector includes a motor that drives a ram, which in turn drives a plunger of a syringe. Unfortunately, the motor and other electronics in the powerhead typically emit radiofrequency (RF) radiation that can detrimentally affect operation of medical equipment, such as a magnetic resonance imaging (MRI) system. In addition, the medical equipment, such as the MRI system, typically emits RF radiation that can detrimentally affect operation of the powerhead. Although existing powered injectors for MRI applications typically include radiation shielding, the detrimental affects of RF radiation can still hinder proper functioning of both the powerhead and the medical equipment.

In addition to the problems with RF radiation, existing powered injectors are generally too large, awkward, or inconvenient to place with the patient inside the magnet bore of the MRI system. Instead, the powerhead is placed outside the magnet bore, and a long run of tubing is used to connect the syringe tip with the injection site. A normal length of tubing may range from about 60 to 90 inches, and may contain as much as 4 to 5 milliliters of fluid. Unfortunately, this volume of fluid remains within the tubing after injecting the fluid from within the syringe, because movement of the syringe plunger cannot inject it into the patient. A typical MRI protocol may prescribe 20 milliliters of contrast agent, leaving about 4 to 5 milliliters of contrast agent (25 percent) within the tubing after the injection. A shortage of 25 percent of the prescribed contrast agent may hinder the image enhancement. MRI contrast agent, such as gadolinium, is very expensive and may be considered cost prohibitive to waste 4 to 5 milliliters of contrast agent per procedure. Existing MRI injectors typically have a second syringe that is filled with a flushing solution, such as saline. At the completion of the contrast injection, the injector chases the contrast agent down the tubing with the saline. This method ensures that the entire volume of contrast agent has been injected into the patient. Thus, only 4 to 5 milliliters of saline has been wasted, which is significantly less expensive than the MRI contrast agent. Unfortunately, the injected volume of saline does not offer any imaging benefits to the patient, while also adding complication, costs, and time to the procedure.

SUMMARY

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

A first aspect of the present invention is directed to a medical fluid injector that includes a fluid drive responsive to pressure of a working fluid (e.g., liquid, pneumatic, or both) to impart a sequence of forces to drive a delivery device (e.g., a syringe) to deliver a medical fluid (e.g., a contrast agent, saline, a radiopharmaceutical, a drug, or a combination thereof). The sequence of forces may be defined as a series of separate and discrete forces, which are generated and/or occur one after another, rather than a single constant force. In other words, the sequence of forces may be defined as a pulse-like sequence or a rhythmic reoccurrence of the forces. The sequence of forces may include peristalsis, which may be described as a rhythmic contraction of a fluid passage to propel a working fluid through the fluid passage. For example, peristalsis may include contraction of the fluid passage in a sequence at one axial position after another along the length of the fluid passage. The sequence of forces also may include pulsatile forces, oscillating forces, stepwise forces, or a combination thereof. For example, the sequence of forces may progressively force a gear to rotate by engaging one tooth after another in discrete steps, e.g., contact a first tooth, push it forward, step to a second tooth, push it forward, and so on. Each force in the sequence may be equal or different. Also, each force in the sequence may be separated in time and/or spatial position.

A second aspect of the invention is directed to a medical fluid injector that includes a multi-fluid drive having a pneumatic drive section (e.g., a piston-cylinder arrangement) coupled to a liquid control section (e.g., a piston-cylinder arrangement). The pneumatic drive section is responsive to pressure of a working pneumatic medium (e.g., air) to induce movement. The liquid control section may include a working liquid (e.g., oil, water, alcohol, etc.) responsive to the movement to control a rate of the movement. This movement may be used to drive a delivery device (e.g., to provide a discharge of medical fluid from the delivery device, for instance when in the form of a syringe).

Yet a third aspect of the invention is directed to a medical fluid injector that includes a multimedia tube that is configured to pass a working fluid (e.g., air) and a light signal (e.g., infrared). The multimedia tube may be capable of sending data, control signals, motive forces, or a combination thereof, based on different types of media (e.g., air, infrared, etc.). Thus, multiple types of media pass through a single tube (e.g., the multimedia tube), thereby reducing the amount of tubing used in an injection procedure. The working fluid may be used by a fluid drive to drive a delivery device (e.g., to provide a discharge of medical fluid from the delivery device, for instance when in the form of a syringe), while the light signal may be used to control a valve, that in turn controls or otherwise has an effect on a flow of the working fluid.

Still a fourth aspect of the invention is directed to a medical fluid injector that includes a peristaltic drive (e.g., sequential movements to drive a fluid) responsive to pressure of a working fluid (e.g., pneumatic, liquid, or both). For example, the peristaltic drive may include a series of mechanisms (e.g., pistons), which sequentially squeeze a tube to create a rhythmic contraction to propel a medical fluid. The pistons may be moved by the working fluid.

A fifth aspect of the invention is directed to a method of operation for a medical fluid injector. The method includes responding to pressure of a working fluid (e.g., pneumatic, liquid, or both) to impart a sequence of forces to drive a delivery device (e.g., syringe, needle, or both) to deliver a medical fluid. For example, a series of control signals or air pulses may cause a series of pistons to apply forces to a fluid passage one after another, thereby creating a rhythmic contraction of the fluid passage to propel the medical fluid along the fluid passage.

Still yet a sixth aspect of the invention is directed to a method of imaging a patient. In this method, a powerhead of a contrast media injector is removably mounted on a patient (e.g., via one or more straps disposed about a limb of the patient). Contrast media is injected into the patient while the powerhead is removably mounted on the patient. Further, the patient is also imaged (e.g., via a magnetic resonance imaging system) while the powerhead is removably mounted on the patient.

Numerous refinements exist of the features noted above in relation to the various aspects of the present invention. Further features may also be incorporated in these various aspects as well. These refinements and additional features may exist individually or in any combination. For instance, various features discussed below in relation to one or more of the illustrated embodiments may be incorporated into any of the above-described aspects of the present invention alone or in any combination. Again, the brief summary presented above is intended only to familiarize the reader with certain aspects and contexts of the present invention without limitation to the claimed subject matter.

BRIEF DESCRIPTION OF THE FIGURES

Various features, aspects, and advantages of the present invention will become better understood when the following detailed description is read with reference to the accompanying figures in which like characters represent like parts throughout the figures, wherein.

DETAILED DESCRIPTION OF SPECIFIC EMBODIMENTS

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a", "an", "the", and "said" are intended to mean that there are one or more of the elements. The terms "comprising", "including", and "having" are intended to be inclusive and mean that there may be additional elements other than the listed elements. Moreover, the use of "top", "bottom", "above", "below" and variations of these terms is made for convenience, but does not require any particular orientation of the components. As used herein, the term "coupled" refers to the condition of being directly or indirectly connected or in contact. Additionally, the phrase "in fluid communication" or "fluidly coupled" indicates that fluid and/or fluid pressure may be transmitted from one object to another.

Figure 1:
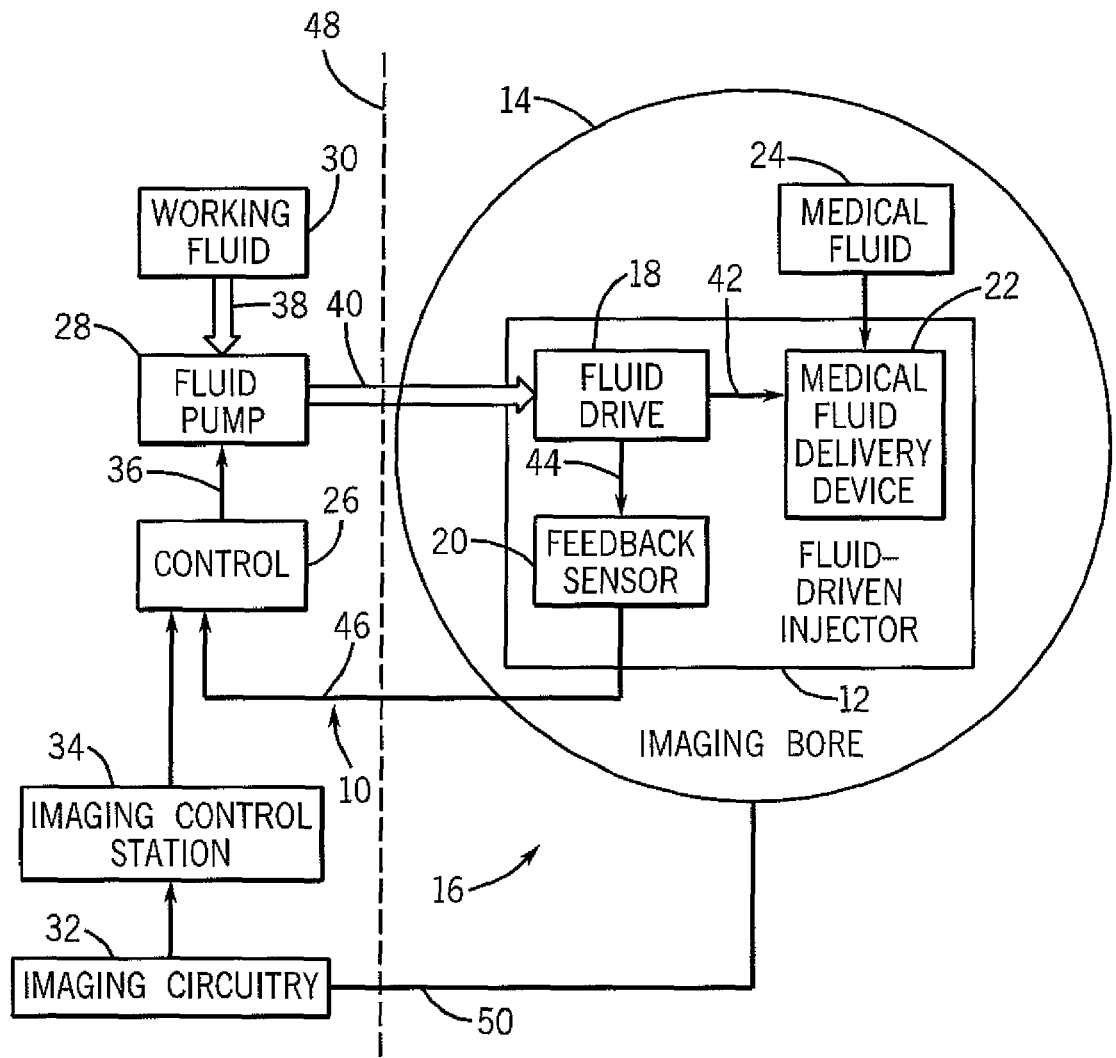
FIG. 1 is a diagram of a fluid driven injector disposed in an imaging bore of an imaging system.

FIG. 1 is a diagram of an exemplary imaging suite 10 having a fluid driven injector 12 disposed within an imaging bore 14 of an imaging system 16. The illustrated injector 12 includes a fluid drive 18, a feedback sensor 20, and a medical fluid delivery device 22. The delivery device 22 receives and/or stores a medical fluid 24 for delivery to a patient positioned within the imaging bore 14 during an imaging procedure. The imaging suite 10 also includes a control 26, a fluid pump 28, and a working fluid 30. The imaging system 16 further includes imaging circuitry 32 coupled to the bore 14, and an imaging control station 34 coupled to the imaging circuitry 32 and the control 26.

In the illustrated embodiment, the imaging suite 10 may operate as a closed loop control system. For example, the control 26 may output a control signal 36 to the fluid pump 28, thereby triggering the pump 28 to receive and transfer a working fluid 30 to the fluid drive 18 as indicated by arrows 38 and 40, respectively. Thus, arrow 36 may represent an electronic, optical, or other appropriate control line; whereas arrows 38 and 40 may represent fluid conduits. For example, the working fluid 30 may include a pneumatic substance, a liquid substance, or a combination thereof. The pneumatic substance may include air, nitrogen, or another suitable non-combustible gas. The liquid may include water, oil, or a suitable hydraulic fluid.

In response to pressure of the working fluid 30, the fluid drive 18 may impart a driving force 42 onto the delivery device 22. For example, the fluid drive 18 may move a piston, a ram, a ratchet and gear assembly, a peristaltic device, or a combination thereof, thereby creating the driving force 42 to displace the medical fluid 24 within the delivery device 22. In certain embodiments, the delivery device 22 may include a syringe having a plunger disposed within a barrel. Thus, the medical fluid 24 may be stored within the syringe until the fluid drive 18 imparts the driving force 42.

The feedback sensor 20 may monitor one or more parameters of the fluid drive 18. For example, the sensor 20 may obtain data relating to a sensed parameter as indicated by arrow 44. The sensed parameter 44 may include a position, velocity, acceleration, temperature, pressure, or other operational characteristic of the fluid drive 18. On some embodiments, the sensor 20 may include a potentiometer (e.g., linear or rotary) or an optical encoder. In turn, the sensor 20 provides a feedback signal 46 to the control 26. Based on the signal 46, the control 26 may increase, decrease, terminate, or maintain output of the pump 28 via the control signal 36. As a result, the imaging suite 10 has proportional, servo feedback control of the fluid driven injector 12.

As illustrated in FIG. 1, the injector 12 and the bore 14 are located in the imaging suite 10 on a first side of a wall 48, while the control 26, the pump 28, the working fluid 30, the imaging circuitry 32, and the control station 34 are disposed in the imaging suite 10 on an opposite side of the wall 48. The wall 48 may include certain shielding materials, such as electromagnetic shielding materials, which may substantially reduce undesirable interference between the imaging bore 14 and the control 26, the fluid pump 28, the circuitry 32, and the station 34. The illustrated injector 12 may be substantially or entirely free of ferrous, or magnetic, or ferromagnetic materials. The injector 12 may be substantially free of electronics, motors, or other devices that may emit or become adversely affected by RF radiation. For example, the fluid drive 18 and the delivery device 22 may be made substantially or entirely of plastics, ceramics, glass, or a combination thereof.

Again, the injector 12 is driven by the fluid pressure of the working fluid 30 supplied by the pump 28. Given that the pump 28 and the control 26 are disposed outside of the room on an opposite side of the wall 48, these components 26 and 28 do not interfere with the imaging bore 14, and vice versa. Instead, only the working fluid 30 may be transferred from one side of the wall 48 to the other, thereby driving the injector 12 in a non-interfering manner with regard to the imaging system 16. In addition, the injector 12 has a relatively compact size and streamlined shape, which is particularly suited for mounting on or near a patient within the imaging bore 14. As a result, the delivery device 22 may be disposed in close proximity to the patient, thereby substantially reducing or eliminating long runs of tubing from the delivery device 22 to the patient. Advantageously, this close proximity may reduce or eliminate the desire for a flushing solution, such as saline.

The illustrated imaging system 16 may be a magnetic resonance imaging (MRI) system or another medical imaging modality. In operation, the circuitry 32 receives and processes data to generate an image of the patient within the imaging bore 14. The control station 34 enables a user to control operation of the imaging circuitry 32, the control 26, or a combination thereof. For example, the user may initiate an injection protocol via the imaging control station 34 as illustrated by arrow 50. As another example, the control station 34 may initiate an imaging protocol via the imaging circuitry 32.

Figure 2:
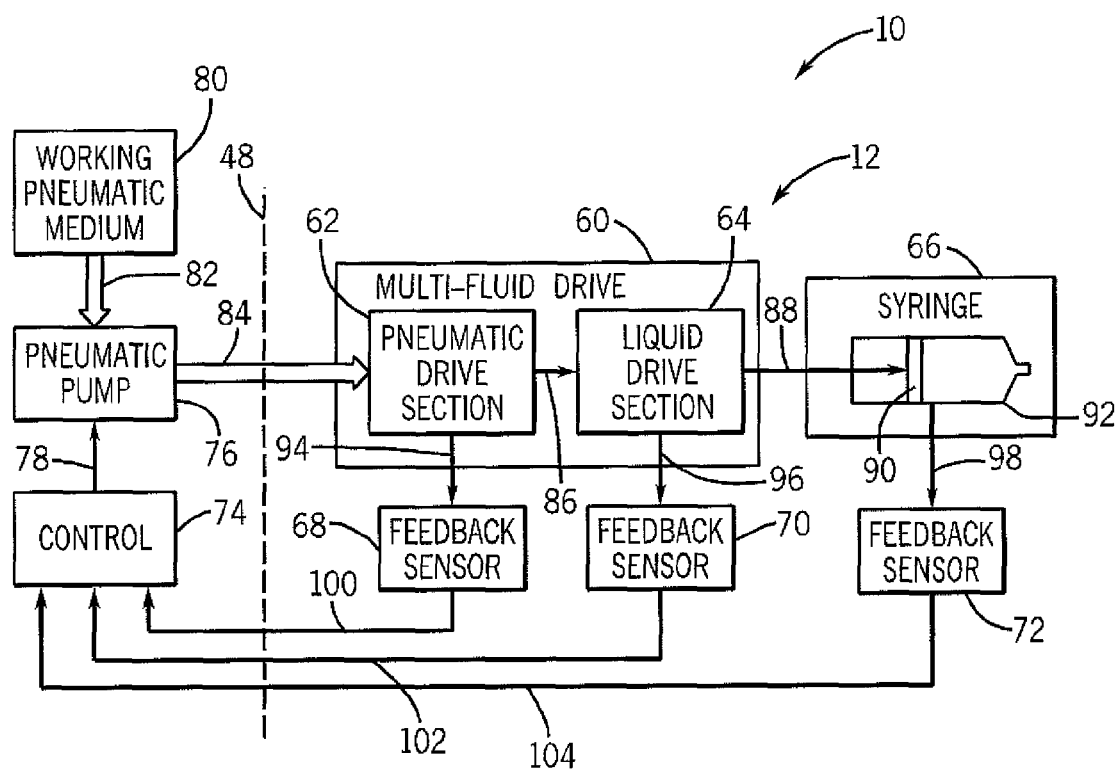
FIG. 2 is a diagram of a fluid driven injector having pneumatic and liquid drive sections.

FIG. 2 is a diagram of another embodiment of the imaging suite 10, wherein the injector 12 has a multi-fluid drive 60. Specifically, the multi-fluid drive 60 may include a pneumatic drive section 62 coupled to a liquid drive section 64. The injector 12 also includes a syringe 66 driven by the multi-fluid drive 60. Furthermore, the system 10 includes feedback sensors 68, 70, and 72 coupled to a control 74, which is in turn coupled to a pneumatic pump 76. In operation, the control 74 provides a control signal 78 to the pump 76, thereby triggering the pump 76 to intake and transfer a working pneumatic medium 80 to the pneumatic drive section 62, as indicated by arrows 82 and 84, respectively. In response to the pneumatic pressure from the pump 76, the pneumatic drive section 62 provides a pneumatic driven pressure or force 86 to the liquid drive section 64, thereby causing the liquid drive section 64 to provide a liquid driven force or pressure 88 onto the syringe 66. Specifically, the liquid drive section 64 may force a plunger 90 to move lengthwise along a barrel 92 of the syringe 66. Advantageously, the working pneumatic medium 80 provides generally clean power to the multi-fluid drive 60, while the liquid working medium disposed in the liquid drive section 64 provides more accurate control of the movement and/or force 88 imparted to the syringe 66.

The feedback sensors 68, 70, and 72 may monitor and obtain data regarding one or more sensed parameters 94, 96, and 98 of the section 62, the section 64, and the plunger 90, respectively. For example, the parameters 94, 96, and 98 may include data regarding position, velocity, acceleration, temperature, pressure, or a combination thereof, which is then transferred to the control 74 as various feedback signals 100, 102, and 104. Thus, similar to the embodiment of FIG. 1, the imaging suite 10 of FIG. 2 can operate as a closed loop control system.

Figure 3:
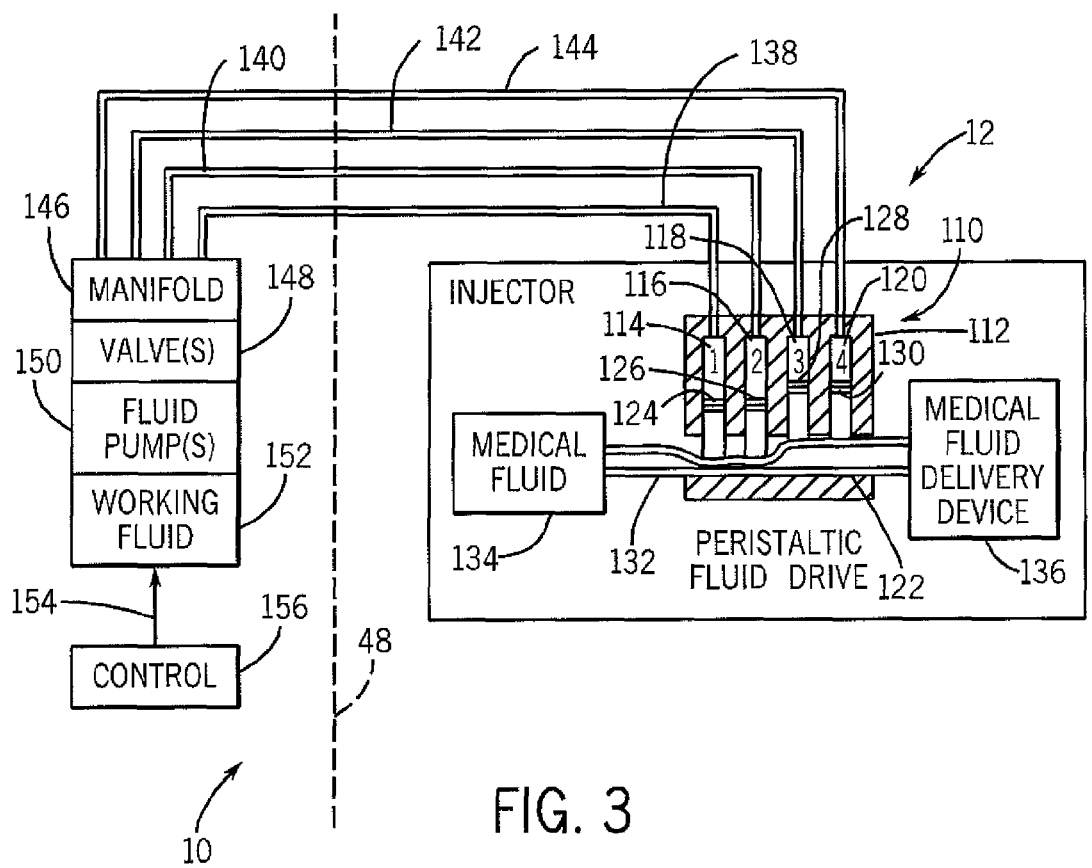
FIG. 3 is a diagram of a fluid driven peristaltic injector.

FIG. 3 is a diagram of another embodiment of the imaging suite 10, wherein the injector 12 includes a peristaltic fluid drive 110 configured to create a sequence of forces to cause peristaltic fluid flow. In the illustrated embodiment, the peristaltic fluid drive 110 may include a cylinder block 112 having a plurality of cylinders 114, 116, 118, and 120 (any appropriate number of cylinders may be utilized by the peristaltic fluid drive 110), which may be arranged generally transverse or perpendicular to a passage 122 (e.g., the cylinders 114, 116, 118, and 120 may be aligned with the passage 122). The peristaltic fluid drive 110 includes a plurality of pistons 124, 126, 128, and 130 disposed in respective cylinders 114, 116, 118, and 120 (e.g., each cylinder includes a corresponding piston). Furthermore, a flexible conduit 132 may extend lengthwise through the passage 122. As illustrated, the pistons 124, 126, 128, and 130 are configured to move upward and downward in a reciprocating manner within the respective cylinders 114, 116, 118, and 120, such that the pistons 124, 126, 128, and 130 open and close the passage 122 in a sequential manner to create a peristaltic wave lengthwise through the passage 122. With the flexible conduit 132 installed within the passage 122, the sequential downward movement (e.g., sequence of forces) of the pistons 124, 126, 128, and 130 onto the flexible conduit 132 creates a rhythmic contraction of the flexible conduit 132 to propel a medical fluid 134 through the peristaltic fluid drive 110 to a medical fluid delivery device 136. In other words, the pistons 124, 126, 128, and 130 produce a series of separate and discrete forces at different times and axial positions along the flexible conduit 132. In this manner, the pistons 124, 126, 128, and 130 create peristaltic fluid flow by contracting the flexible conduit 132 in a sequence at one axial position after another along the length of the flexible conduit 132. In certain embodiments, the medical fluid 134 may include a drug, a contrast agent, a radiopharmaceutical, saline, or a combination thereof. Moreover, the delivery device 136 may include a hollow injection needle, a short run of tubing, or another suitable injection device.

The sequential movement of the pistons 124, 126, 128, and 130 may be achieved by one or more fluid conduits coupled to one or more fluid pumps disposed on an opposite side of the wall 48 from the injector 12. For example, in the illustrated embodiment, the imaging suite 10 may include fluid conduits 138, 140, 142, and 144 coupled to the respective cylinders 114, 116, 118, and 120, and a manifold 146. The manifold 146 may include or couple with one or more valves 148 and one or more fluid pumps 150. For example, the imaging suite 10 may include a single fluid pump 150 and valves 148 corresponding to the number of pistons and cylinders of the fluid drive 110 (four in the illustrated embodiment). Alternatively, the imaging suite 10 may include fluid pumps 150 and valves 148 corresponding to the number of pistons and cylinders of the fluid drive 110 (four in the illustrated embodiment).

The fluid pump(s) 150 may intake and deliver a working fluid 152 in response to one or more control signals 154 from a control 156. In response to the control signal(s), the fluid pump(s) 150 and valves 148 cooperate to supply the working fluid 152 in sequential pulses one after another to the respective cylinders 114, 116, 118, and 120, thereby causing the pistons 124, 126, 128, and 130 to sequentially compress the flexible conduit 132 disposed within the passage 122. Similar to the embodiments of FIGS. 1 and 2, the illustrated peristaltic fluid drive 110 may be non-magnetic, non-ferrous, or a combination thereof. Thus, the fluid drive 110 does not interfere or become detrimentally impacted by RF radiation or magnetics associated with the MRI system.

Figure 4:
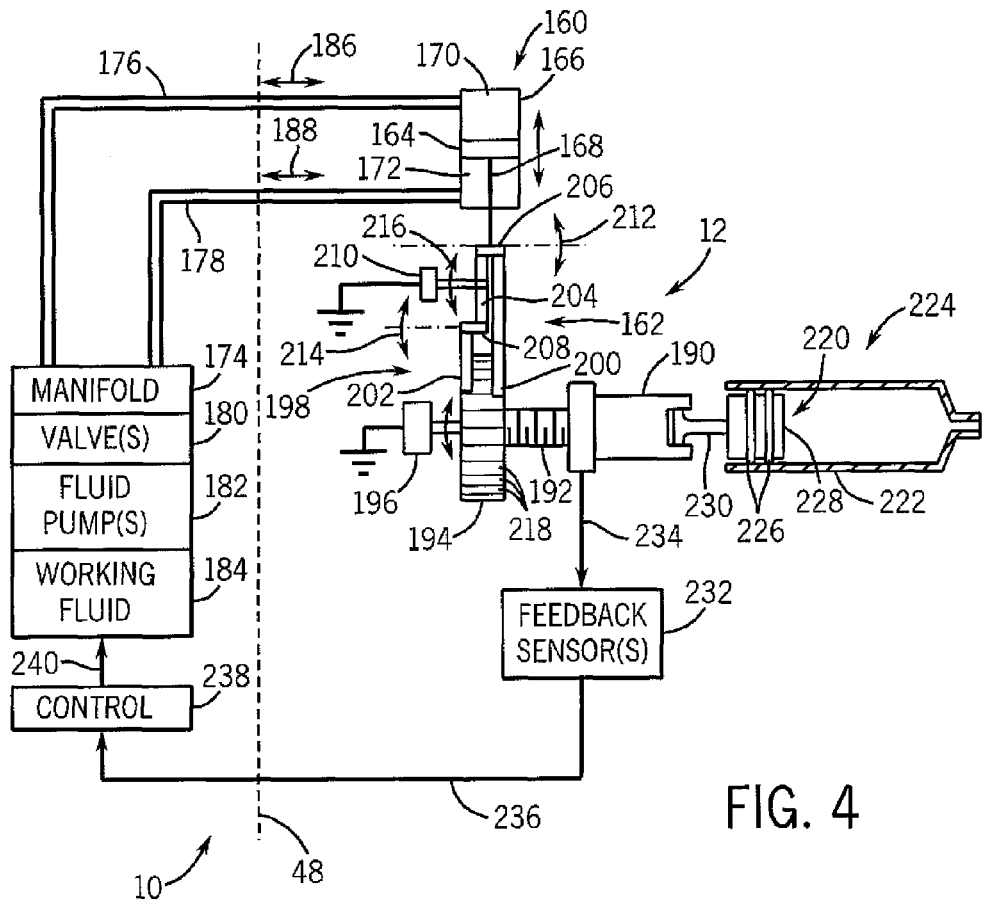
FIG. 4 is a diagram of an injector having a fluid driven ratchet and gear assembly.

FIG. 4 is a diagram of an alternative embodiment of the imaging suite 10, wherein the injector 12 includes a fluid drive 160 coupled to a gear and ratchet assembly 162 to create a sequence of forces. The illustrated fluid drive 160 may include a piston 164 disposed moveably within a cylinder 166, wherein the piston 164 is coupled to a rod 168. The illustrated piston 164 divides the cylinder 166 into a first chamber 170 and a second chamber 172, which are coupled to a manifold 174 via respective first and second conduits 176 and 178. Similar to the embodiment of FIG. 3, the manifold 174 may include or couple with one or more valves 180 and one or more fluid pumps 182, such that a working fluid 184 can be forced to flow in a reciprocating manner to the first and second chambers 170 and 172 via the first and second conduits 176 and 178. For example, as the working fluid 184 flows from the manifold 174 toward the first chamber 170, the working fluid flows from the second chamber 172 toward the manifold 174. Upon reversing the direction of the piston 164, the working fluid 184 flows from the manifold 174 into the second chamber 172, while the working fluid 184 flows from the first chamber 170 toward the manifold 174. Arrows 186 and 188 illustrate this reciprocating flow within the first and second conduits 176 and 178. As a result of this reciprocating flow, the piston 164 and the rod 168 move in a reciprocating manner (upward and downward in the view shown in FIG. 4) within the cylinder 166, thereby imparting a reciprocating force on the gear and ratchet assembly 162.

The gear and ratchet assembly 162 may include a ram 190, a ball screw 192 coupled to the ram 190, a gear 194 coupled to the ball screw 192, one or more bearings 196 coupled to the gear 194 and/or the ball screw 192, and a ratchet assembly 198. The ratchet assembly 198 may be configured to progressively engage the gear 194 in a stepwise manner in response to reciprocating motion of the rod 168. The ratchet assembly 198 may include a first arm 200, a second arm 202, and a third arm 204 disposed between the first and second arms 200 and 202. Moreover, the third arm 204 may rotatably couple with both the first and second arms 200 and 202 at rotational joints 206 and 208. Finally, the third arm 204 may couple to a bearing 210. As a result, the first arm 200 can rotate about the rotational joint 206 as indicated by arrow 212, the second arm 202 can rotate about the rotational joint 208 as indicated by arrow 214, and the third arm 204 can rotate relative to the bearing 210 as illustrated by arrow 216. Each of the first arm 200 and second arm 202 may be characterized as ratchets of the ratchet assembly 198.

In response to the reciprocating motion of the rod 168, the first and second arms 200 and 202 may reciprocate forward and backward to step along and sequentially push teeth 218 of the gear 194 with a sequence of forces, thereby progressively driving the gear 194 to rotate the ball screw 192. Again, the sequence of forces may be defined as a series of separate and discrete forces, which are generated and/or occur one after another rather than a single constant force. In the illustrated embodiment, for example, the sequence of forces applied by the first and second arms 200 and 202 may progressively force the gear 194 to rotate by engaging one tooth 218 after another in discrete steps, e.g., contact a first tooth 218, push it forward, step to a second tooth 218, push it forward, and so on. As the ball screw 192 rotates, the ram 190 may be forced to translate a plunger 220 disposed within a barrel 222 of a syringe 224. Specifically, the plunger 220 may include a plurality of seals disposed about a plunger head 228, which is coupled to a drive shaft 230 leading to the ram 190.

The imaging suite 10 illustrated in FIG. 4 may include one or more feedback sensors 232 configured to monitor a position, velocity, acceleration, or a combination thereof, of the ram 190, as indicated by arrow 234. In turn, the one or more sensors 232 may provide a feedback signal 236 to a control 238, which may provide a closed loop control signal 240 to the fluid pumps 182. Similar to the embodiments described above, the illustrated injector 12 may be substantially or entirely free from ferrous materials, magnetic materials, or a combination thereof. In addition, the illustrated injector 12 may be substantially or entirely free of electronics or other components that may potentially emit RF radiation, magnetic fields, or other potential interference with the MRI system. Again, the illustrated control 238, the fluid pumps 182, and any ferrous or magnetic materials may be disposed on an opposite side of the wall 48 relative to the fluid driven injector 12.

Figure 5:
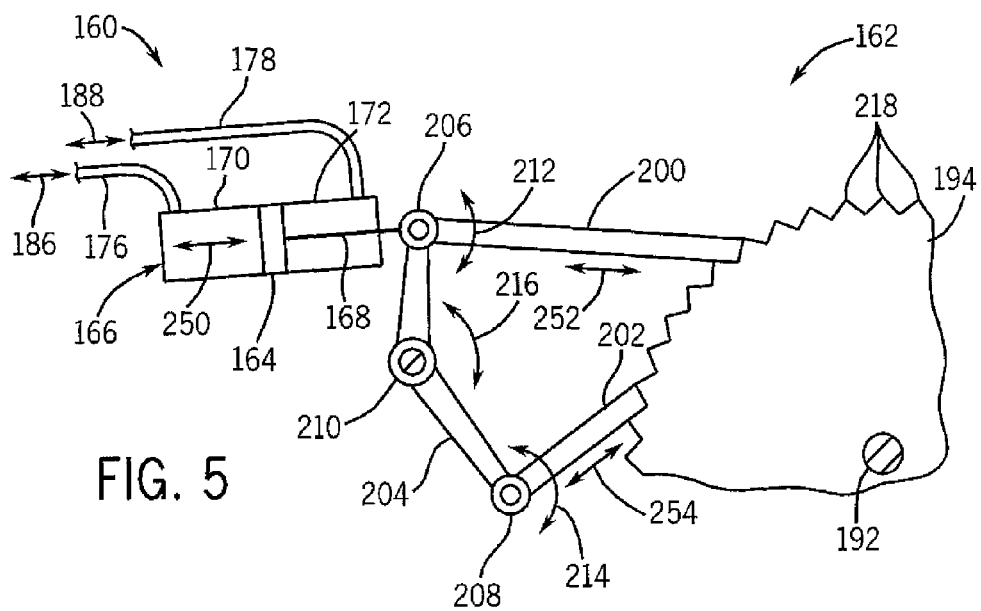
FIG. 5 is a partial view of the ratchet and gear assembly of FIG. 4.

FIG. 5 is a diagram of a partial view of the fluid drive 160 coupled to the gear and ratchet assembly 162 of the embodiment of FIG. 4. As illustrated, the opposite reciprocating flows 186 and 188 through the conduits 176 and 178 to/from the first and second chambers 170 and 172 cause the piston 164 and the rod 168 to reciprocate inwardly and outwardly as indicated by arrow 250. In response to this reciprocating movement 250, the rod 168 causes the third arm 204 to rotate in a reciprocating manner about the bearing 210 as illustrated by arrow 216. In turn, the reciprocating rotation 216 of the third arm 204 causes the first and second arms 200 and 202 to reciprocate forward and backward relative to the gear 194 as indicated by arrows 252 and 254. For example, as the first arm 200 moves forward toward the gear 194, the second arm 202 moves away from the gear 194. The reverse is also true. As the second arm 202 moves toward the gear 194, the first arm 200 moves away from the gear 194. During these reciprocating movements, one of the first and second arms 200 and 202 pushes against one of the teeth 218 on the gear 194, as the other one of the arms withdraws and falls into a subsequent tooth 218 on the gear 194. Thus, the first and second arms 200 and 202 alternate between a forward motion pushing against the teeth 218 to drive the gear 194 and a reverse motion stepping into a subsequent tooth 218, thereby creating a sequence of forces to rotate the gear 194 in a stepwise manner. Again, the sequence of forces may be defined as a series of separate and discrete forces, which are generated and/or occur one after another rather than a single constant force. In the present embodiment, the sequence of forces may progressively force the gear 194 to rotate by engaging one tooth 218 after another in discrete steps, e.g., contact a first tooth 218, push it forward, step to a second tooth 218, push it forward, and so on. Each force in the sequence may be equal or different. Also, each force in the sequence may be separated in time and/or spatial position. Again, the components of the fluid drive 160 and the gear and ratchet assembly 162 may be substantially or entirely free of ferrous materials, magnetic materials, and components that may emit or be adversely affected by RF radiation, magnetics, and so forth.

Figure 6:
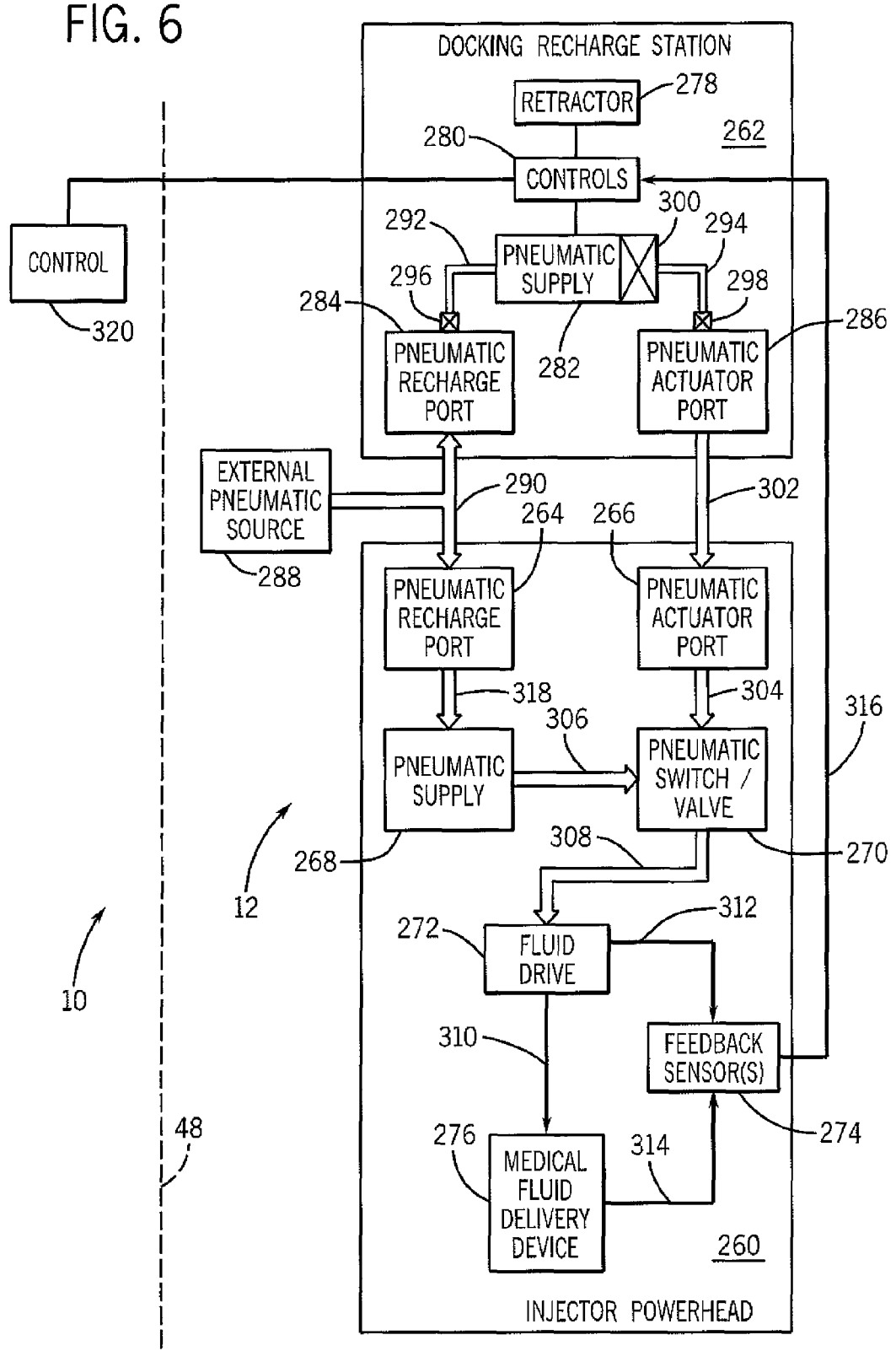
FIG. 6 is a diagram of a fluid driven injector having a docking recharge station.

FIG. 6 is a diagram of an alternative embodiment of the imaging suite 10, wherein the injector 12 includes an injector powerhead 260 configured to mate with a docking recharge station 262. The illustrated powerhead 260 may include a pneumatic recharge port 264, a pneumatic actuator port 266, a pneumatic supply 268, a pneumatic switch/valve 270, a fluid drive 272, one or more feedback sensors 274, and a medical fluid delivery device 276. The station 262 may include a retractor 278, one or more controls 280, a pneumatic supply 282, a pneumatic recharge port 284, and a pneumatic actuator port 286, The injector 12 may include an external pneumatic source 288 configured to supply a pneumatic working medium to the port 264, the port 284, or a combination thereof, via one or more removable conduits 290. Thus, the source 288 may replenish the pneumatic supplies 268 and 282 via the ports 264 and 284. The ports 284 and 286 may be coupled to the supply 282 via conduits 292 and 294. The conduits 292 and 294 may include one or more valves, such as check valves 296 and 298, to control the pneumatic flow. The pneumatic supply 282 may include one or more valves to control the pneumatic flow to and from the ports 284 and 286. For example, the illustrated supply 282 may include a valve 300 configured to open and close the pneumatic flow through the conduit 294 and the port 286. For example, the valve 300 may be controlled by the one or more controls 280. The controls 280 may include a valve actuator, a flow meter, or a combination thereof.

The powerhead 260 may be configured to operate separate from or connected with the station 262. For example, the port 286 may removably couple with the port 266 via a pneumatic conduit 302. The conduit 302 may supply the pneumatic working medium from the supply 282 to the fluid drive 272 via the valve 270. However, in the illustrated embodiment, the fluid drive 272 receives the pneumatic working medium from the local pneumatic supply 268, while the valve 270 opens and closes in response to pneumatic pressure supplied through the port 266. In other words, the valve 270 is actuated by a pneumatic pressure provided by the station 262, while the actual pneumatic working medium is stored locally within the supply 268. Thus, the port 266 provides a pneumatic control pressure to the valve 270 via a conduit 304. Upon opening the valve 270 in response to pneumatic control pressure, the pneumatic working medium in the supply 268 flows through conduits 306 and 308 to the fluid drive 272. In turn, the fluid drive 272 responds to the pneumatic pressure from the supply 268 to impart a driving force 310 on the delivery device 276. During operation of the powerhead 260, one or more feedback sensors 274 may monitor conditions 312 and 314 of the fluid drive 272 and the delivery device 276, and provide feedback signals 316 to the control(s) 280 in the station 262.

After the powerhead 260 completes an injection of medical fluid, the pneumatic supply 268 may be recharged by the source 288. The pneumatic medium may pass through the port 264, through a conduit 318, and into the supply 268. In addition, the retractor 278 disposed on the station 262 may be used to retract the position of the fluid drive 272 for a subsequent injection. For example, the retractor 278 may include a manual or powered retractor, which can retract a ram into a pre-injection position. The illustrated imaging suite 10 of FIG. 6 may include a control 320 disposed on an opposite side of the wall 48 relative to the injector 12. Again, the powerhead 260 and the station 262 may be substantially or entirely free of ferrous materials, magnetic materials, and electronics that potentially generate or become adversely affected by RF radiation, magnetics, and so forth. However, in some embodiments, the control(s) 280 and/or the valve 300 may include electronics that generally do not operate during an imaging procedure of the MRI system.

Figure 7:
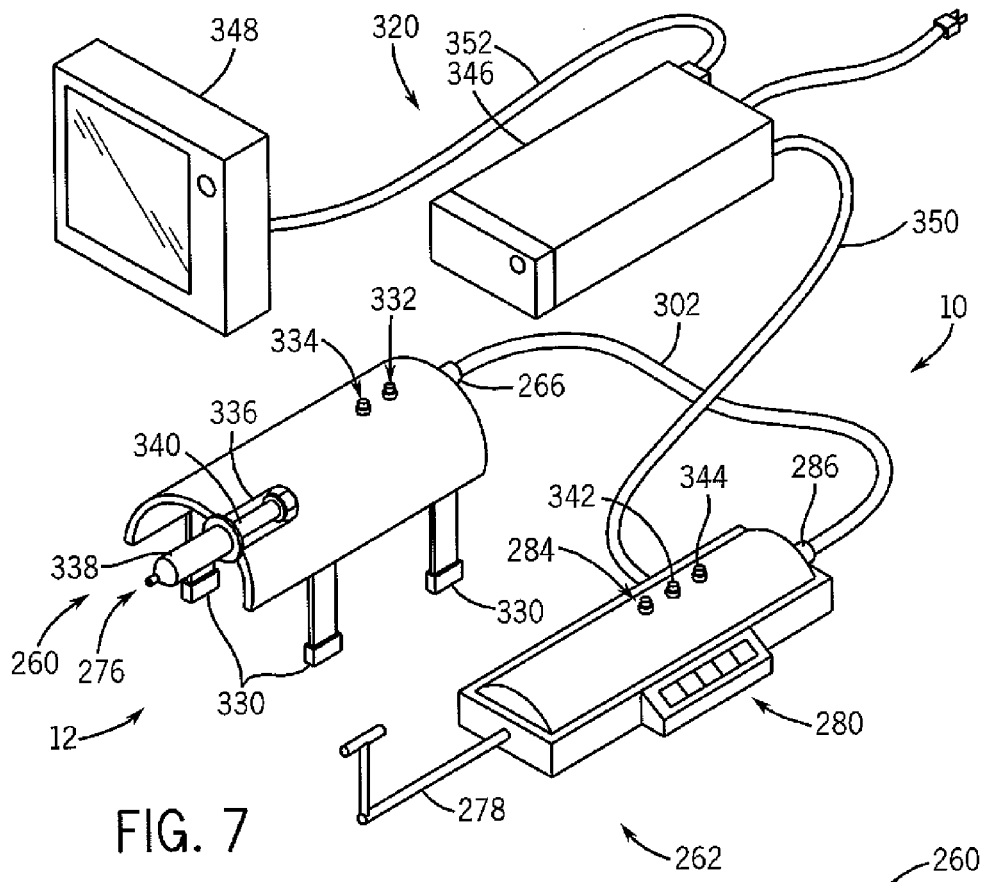
FIG. 7 is a diagram of an embodiment of the injector and station of FIG. 6.

FIG. 7 is a diagram of an embodiment of the powerhead 260 and station 262 of FIG. 6, further illustrating structural characteristics of these components 260 and 262. In the illustrated embodiment, the powerhead 260 may include a plurality of patient body mounts, such as arm/leg straps 330. These straps 330 may be coupled together via buttons, clips, hook-and-loop material, buckles, and/or other appropriate manners of coupling. The powerhead 260 may be described as a patient mountable injector (e.g., removably mounted), which is particularly well suited for placement with the patient inside the imaging bore 14 as discussed above with reference to FIG. 1. One of the benefits of a patient mountable injector is that less tubing may be required for an injection than with a conventional injector that is mounted on a stand, wall, or ceiling. The illustrated powerhead 260 includes a flow adjuster 332 and a syringe adjuster 334. Furthermore, the powerhead 260 includes a syringe receptacle 336 configured to support a syringe 338. As discussed above with reference to FIG. 6, the fluid drive 272 disposed within the powerhead 260 is responsive to a pneumatic pressure to drive a plunger 340 of the syringe 338. The fluid drive 272 may be triggered by a pneumatic pulse or pressure supply from the station 262 through a conduit 302 to the powerhead 260. Moreover, the control 280 disposed on the station 262 may be used to control various aspects of the powerhead 260. The station 262 may include flow valve adjusters or adjustment connections 342 and 344. Finally, the illustrated retractor 278 may be a manual retractor mechanism, which can be inserted into the syringe receptacle 336 to force a ram of the fluid drive 272 back into a pre-injection position. Alternatively, the retractor 278 may have a pressure or motor-assisted mechanism to force the ram of the powerhead 260 back into a pre-injection position. The illustrated station 262 may be coupled to a main control 346 and user interface 348 of the control 320 via electrical cables 350 and 352. However, the main control 346 and user interface 348 may be configured to not operate during an injection procedure with the powerhead 260. Therefore, the powerhead 260 and station 262 would do not interfere with operation of the MRI system.

Figure 8:
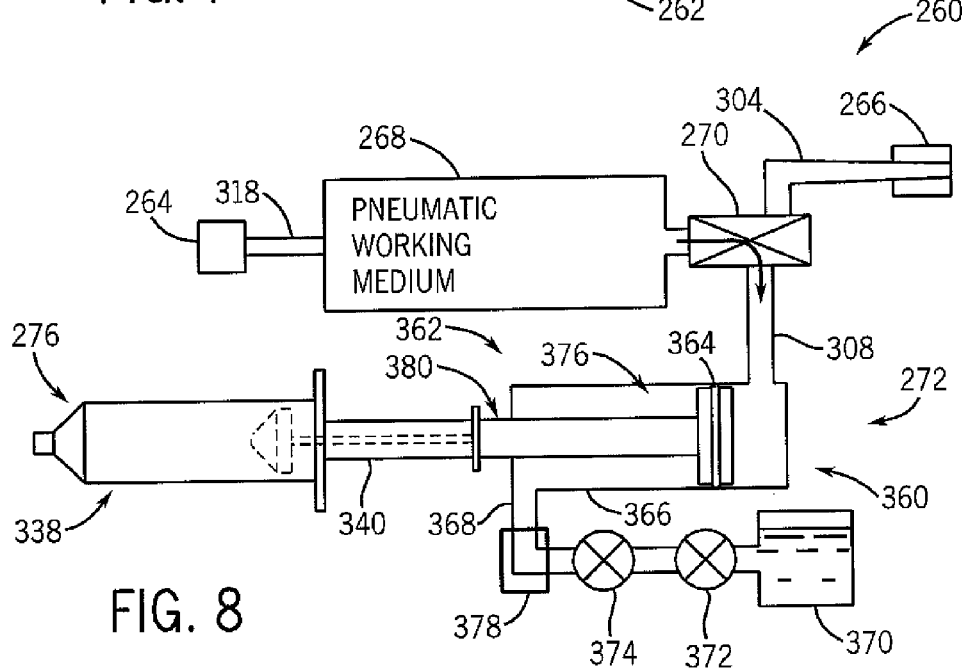
FIGS. 8 and 9 are diagrams of alternative fluid driven injectors having pneumatic and liquid drive sections.

FIG. 8 is a diagram of an exemplary embodiment of the powerhead 260 of FIGS. 6 and 7, further illustrating a multi-fluid configuration of the fluid drive 272 similar to the embodiment described above with reference to FIG. 2. In the illustrated embodiment, the fluid drive 272 includes a pneumatic drive section 360 coupled to a liquid drive section 362. Specifically, the sections 360 and 362 may be divided by a piston 364 disposed movably (e.g., capable of sliding back and forth, or in a reciprocating fashion) within a cylinder 366. The liquid drive section 362 may include a conduit 368 leading to a reservoir 370, wherein a plurality of valves 372 and 374 are disposed between the reservoir 370 and the piston 364 to control flow of a liquid 376 toward the reservoir 370 during movement of the piston 364. The conduit 368 also may include a pump 378 configured to force the fluid to flow between the liquid drive section 362 and the reservoir 370, as discussed further below. The piston 364 may be coupled to a ram 380, which is configured to drive the plunger 340 into the syringe 338.

In the embodiment of FIG. 8, the pneumatic working medium disposed within the supply 268 may provide pressure to move the piston 364 upon opening the valve 270 in response to the pneumatic control pressure provided through the port 266. Thus, the pneumatic working medium forces the piston 364 to move the ram 380 against the plunger 340, while the liquid 376 within the liquid drive section 362 provides accurate control of the movement of the piston 364 via the valves 372 and 374. For example, the valves 372 and 374 may be adjusted or set by the station 262, thereby controlling the flow rate of the liquid 376 to the reservoir 370. In this manner, the liquid pressure within the section 362 at least partially opposes the pneumatic pressure in the pneumatic drive section 360, thereby slowing down the movement of the piston 364 to provide a controlled injection with the syringe 338. Upon completing an injection, the pump 378 may be engaged by the station 262, such that the liquid pressure overcomes the air pressure to return the piston 364 to a pre-injection state. In the illustrated embodiment of FIG. 8, the fluid drive 272 is substantially or entirely non-ferrous, non-magnetic, and without electronics.

Figure 9:
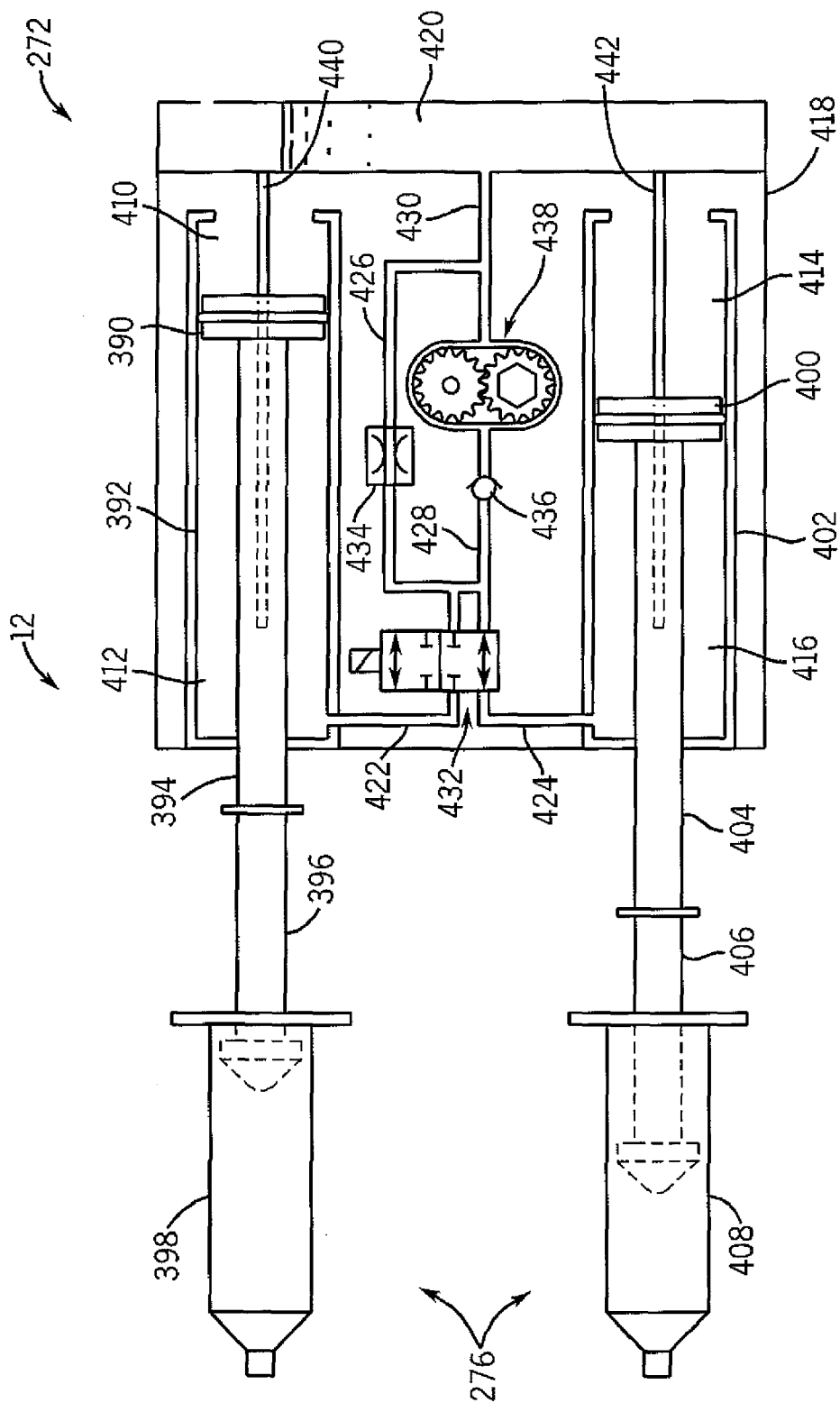

FIG. 9 is a diagram of an alternative embodiment of the fluid drive 272 of FIGS. 6-8, illustrating a dual-syringe configuration driven by a multi-fluid drive assembly. Specifically, the fluid drive 272 of FIG. 9 may include a first piston 390 disposed moveably along a first cylinder 392, such that a first ram 394 can move a first plunger 396 in a first syringe 398. The fluid drive 272 includes a second piston 400 disposed moveably within a second cylinder 402, such that a second ram 404 can move a second plunger 406 in a second syringe 408. The first piston 390 divides the first cylinder 392 into a first pneumatic chamber 410 and a first liquid chamber 412. Similarly, the second piston 400 divides the second cylinder 402 into a second pneumatic chamber 414 and a second liquid chamber 416. The first and second pneumatic chambers 410 and 414 may be separated from one another or in fluid communication with one another. For example, in the illustrated embodiment, the chambers 410 and 414 are part of a common pneumatic chamber 418. In some embodiments, the chamber 418 is open to atmosphere, whereas other embodiments of the chamber 418 are under a suitable pressure to provide a driving force against the first and second pistons 390 and 400.

The fluid drive 272 includes a liquid reservoir 420 in fluid communication with the first and second liquid chambers 412 and 416. The illustrated reservoir 420 may be coupled to the first and second chambers 412 and 416 via one or more liquid conduits 422, 424, 426, 428, and 430, which may include various valves, pumps, or a combination thereof. For example, the illustrated conduits 422 and 424 may include a piezoelectric selector valve 432 to control liquid flow from the chamber 412, or the chamber 416, or both, to the liquid reservoir 420 via subsequent conduits. The conduit 426 may include a piezoelectric servo valve 434 configured to provide speed control of the liquid flow between the chambers 412 and 416 and the reservoir 420. The conduit 428 may include a check valve 436 and a gear pump 438 to provide liquid from the reservoir 420 back to the chamber 412, the chamber 416, or both. Thus, the check valve 436 may restrict flow from the chambers 412 and 416 toward the reservoir 420, while permitting the reverse flow from the reservoir 420 to the chambers 412 and 416.

The fluid drive 272 may include first and second position sensors 440 and 442 configured to sense the position of the first and second pistons 390 and 400, respectively. Thus, the position sensed by the sensors 440 and 442 may be used to control the movement of the first and second pistons 390 and 400 via the piezoelectric servo valve 434. In other embodiments, the valves 432 and 434 may be replaced with other suitable valve assemblies, such as pneumatically controlled valves, optically controlled valves, and so forth.

Again, the pneumatic pressure within the chamber 418 generally drives the pistons 390 and 400. The liquid pressure within the chambers 412 and 416 generally regulates the movement of the pistons 390 and 400, thereby providing accurate motion control of the plungers 396 and 406 into the respective syringes 398 and 408. Moreover, the illustrated fluid drive 272 may be substantially or entirely free of ferrous materials, magnetic materials, or a combination thereof. Thus, the injector 12 is particularly well suited for operation with the MRI system, and is relatively compact and patient mountable for placement within the imaging bore 14 as discussed above with reference to FIG. 1.

Figure 10:
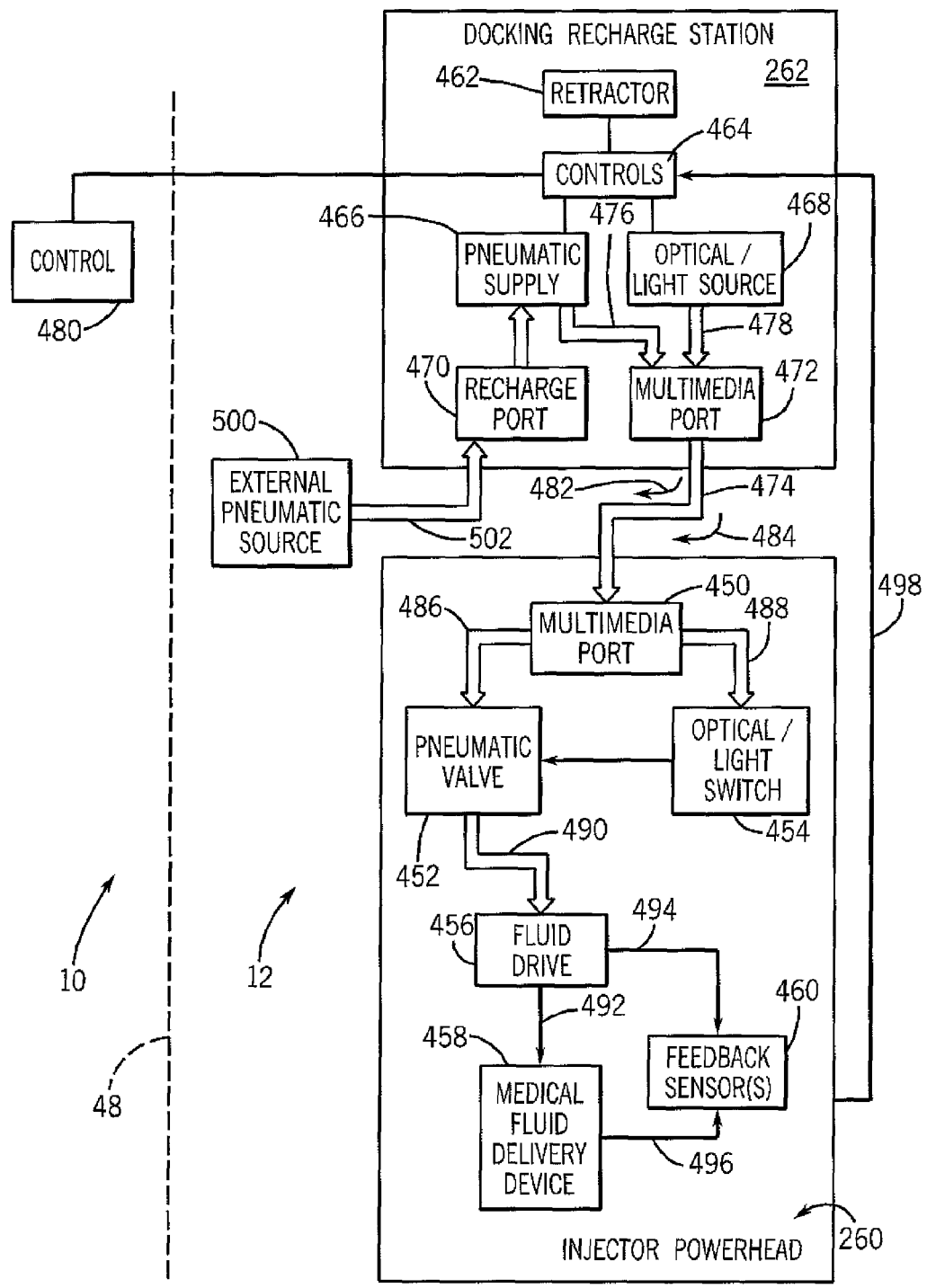
FIG. 10 is a diagram of a fluid driven injector coupled to a docking recharge station via a multimedia tube.

FIG. 10 is a diagram of an alternative embodiment of the imaging suite 10 of FIG. 6, wherein the powerhead 260 and the station 262 are configured with fiber optics in combination with pneumatic controls. Specifically, the powerhead 260 may include a multimedia port 450, a pneumatic valve 452, an optical/light switch 454, a fluid drive 456, a medical fluid delivery device 458, and one or more feedback sensors 460. The station 262 may include a retractor 462, one or more controls 464, a pneumatic supply 466, an optical/light source 468, a recharge port 470, and a multimedia port 472. In addition, the injector 12 includes a multimedia conduit 474 removably coupled to the ports 450 and 472.

In the illustrated embodiment, the multimedia conduit 474 is configured to transmit both a pneumatic working medium and an optical/light signal between the ports 450 and 472. Specifically, the port 472 may receive the pneumatic working medium from the supply 466 via a conduit 476 and a signal from the source 468 via a conduit 478. These transmissions may be initiated by the control(s) 464 and/or user interaction with a control 480. Thus, the pneumatic working medium and the optical/light signal may be simultaneously transmitted through the conduit 474 as indicated by arrows 482 and 484. Upon receipt at the port 450, the pneumatic working medium may be transmitted to the valve 452 via a conduit 486, while the optical/light signal may be transmitted to the switch 454 via a conduit 488.

In turn, the switch 454 generally controls operation of the valve 452. For example, the signal 484 may trigger the switch 454 to open or close the valve 452, thereby controlling flow of the pneumatic working medium 482 toward the fluid drive 456 via conduit 490. The pneumatic pressure supplied to the fluid drive 456 then creates a driving force or pressure 492, which drives a medical fluid from the medical fluid delivery device 458 and into the patient. During operation, the sensor(s) 460 may monitor conditions 494 and 496 of the fluid drive 456 and the delivery device 458, and provide feedback signal(s) 498 to the control(s) 464. Similar to the embodiment of FIG. 6, the recharge port 470 may receive an additional supply of the pneumatic working medium from an external pneumatic source 500 through a conduit 502. Advantageously, the multimedia conduit 474 enables transmission of different types of media to provide both power and control functions simultaneously between the station 262 and the powerhead 260.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cap all modifications, equivalents, and alternatives falling within the spirit and scope of the invention as defined by the following appended claims.

The invention claimed is:

1. A medical fluid injector for use in an MRI procedure comprising: a pneumatic working medium supply; a cylinder; a piston disposed within said cylinder; a pneumatic working medium within said cylinder on a first side of said piston, wherein said pneumatic working medium supply is connectable with said cylinder on said first side of said piston; a liquid within said cylinder on a second side of said piston opposite of said first side, wherein a substantially non-ferrous and substantially non-magnetic fluid drive that is configured to not interfere with magnetic resonance imaging comprises said cylinder, said piston, said pneumatic working medium within said cylinder on said first side of said piston, and said liquid within said cylinder on said second side of said piston; a liquid reservoir connectable with said cylinder on said second side of said piston; a first valve between said liquid reservoir and said cylinder on said second side of said piston; a pump located between said liquid reservoir and said cylinder on said second side of said piston, and configured to force liquid to flow between said cylinder on said second side of said piston and said liquid reservoir; and a ram coupled to said piston, wherein said pneumatic working medium on said first side of said piston moves said piston in an injection direction to move said ram as said liquid within said cylinder on said second side of said piston opposes movement of said piston.

2. The medical fluid injector of claim 1, wherein said pneumatic working medium supply comprises a pneumatic pump.

3. The medical fluid injector of claim 1, further comprising a valve disposed between said pneumatic working medium supply and said cylinder on said first side of said piston.

4. The medical fluid injector of claim 1, further comprising first and second valves between said liquid reservoir and said cylinder on said second side of said piston.

5. The medical fluid injector of claim 4, further comprising a pump located between liquid reservoir and said cylinder on said second side of said piston, and configured to force liqud to flow between said cylinder on said second side of said piston and said liquid reservoir.

6. The medical fluid injector of claim 1, wherein said pneumatic working medium supply and said liquid reservoir are independent of one another.

7. The medical fluid injector of claim 1, wherein there is a single shared fluid boundary between said pneumatic working medium and said liquid, and wherein said single shared fluid boundary is said piston.

8. The medical fluid injector of claim 1, further comprising a powerhead, wherein said powerhead comprises said pneumatic working medium supply, said cylinder, and said piston.

9. The medical fluid injector of claim 1, further comprising a powerhead, wherein said powerhead comprises said cylinder and said piston, and wherein said pneumatic working medium supply is located outside of said powerhead.

* * * * *